US008152816B2

(12) United States Patent
Tuma et al.

(10) Patent No.: US 8,152,816 B2
(45) Date of Patent: Apr. 10, 2012

(54) COMPUTER-ASSISTED PLANNING METHOD FOR CORRECTING CHANGES IN THE SHAPE OF JOINT BONES

(75) Inventors: Gregor Tuma, München (DE); Florian Schindler, Affoltern am Albis (CH); Marc Fricke, Feldkirchen (DE); Martin Haimerl, Gilching (DE)

(73) Assignee: Brainlab AG, Feldkirchen (DE)

( * ) Notice: Subject to any disclaimer, the term of this patent is extended or adjusted under 35 U.S.C. 154(b) by 972 days.

(21) Appl. No.: 12/138,223

(22) Filed: Jun. 12, 2008

(65) Prior Publication Data

US 2008/0319449 A1 Dec. 25, 2008

Related U.S. Application Data

(60) Provisional application No. 60/951,281, filed on Jul. 23, 2007.

(30) Foreign Application Priority Data

Jun. 15, 2007 (EP) .................................... 07110358

(51) Int. Cl.
*A61B 5/103* (2006.01)

(52) U.S. Cl. ....................................... 606/102; 382/131

(58) Field of Classification Search .................. 606/102; 382/131; 703/6
See application file for complete search history.

(56) References Cited

U.S. PATENT DOCUMENTS

| | | | |
|---|---|---|---|
| 4,936,862 A * | 6/1990 | Walker et al. ................. | 128/898 |
| 5,871,018 A | 2/1999 | Delp et al. | |
| 6,711,432 B1 | 3/2004 | Weiss et al. | |
| 8,014,984 B2 * | 9/2011 | Iannotti et al. .................... | 703/6 |
| 2006/0241388 A1 | 10/2006 | Lavallee | |

FOREIGN PATENT DOCUMENTS

| | | |
|---|---|---|
| DE | 100 57 023 A1 | 6/2002 |
| WO | WO 01/35842 | 5/2001 |

* cited by examiner

*Primary Examiner* — Ralph Lewis
(74) *Attorney, Agent, or Firm* — Renner, Otto, Boisselle & Sklar, LLP

(57) ABSTRACT

The patent discloses a system and method for correcting changes in the shape of joint bones in a bone joint, including: providing a three-dimensional imaging data set of a bone joint; identifying the joint bones in the data set based on the shapes of the joint bones; inscribing a portion of a joint bone to be reconstructed with a base shape; determining contour deviations of the inscribed joint bone from the base shape by ascertaining contour distances between the base shape and the shape of the inscribed joint bone in different incision planes; determining a three-dimensional deviating volume using the contour deviations; and using the deviating volume for correction planning.

23 Claims, 3 Drawing Sheets

COMPUTER-ASSISTED PLANNING METHOD FOR CORRECTING CHANGES IN THE SHAPE OF JOINT BONES

RELATED APPLICATION DATA

This application claims priority of U.S. Provisional Application No. 60/951,281 filed on Jul. 23, 2007, and EP 07110358 filed on Jun. 15, 2007, which are incorporated herein by reference in their entirety.

FIELD OF THE INVENTION

The invention relates to a system and method for computer-assisted planning to correct changes in the shape of joint bones.

BACKGROUND OF THE INVENTION

Changes in the shape of joint bones are a possible cause of arthritic joint diseases. Bone anomalies can occur in the region of the pelvic joint and can lead to bone interferences in the joint region. When the leg moves over time these interferences can cause bone surfaces to wear. Computer-assisted planning can be used to prepare reconstruction treatments that restore a suitable bone shape. Computer-assisted planning has been based on determining the contour of joint bones on a two-dimensional basis (for example, in a particular incision plane). The reference "Journal of Bone and Joint Surgery", Volume 84-B, No. 4, May 2002, pages 556 to 560, Nötzli et al. discloses determining a contour of a femoral neck, in which a measurement system and/or angle system is specified. Nötzli et al. is incorporated herein by reference in its entirety.

SUMMARY OF THE INVENTION

A method in accordance with the invention enables a computer to assist and plan for correcting changes in the shape of a joint bone (or the shapes of joint bones) and may include one or more of the following steps:
  providing a three-dimensional imaging data set of a bone joint having joint bones;
  identifying the joint bones in the data set based on shapes of the joint bones in the data set and typical joint bone shapes;
  inscribing a portion of a joint bone to be reconstructed with an assignable base shape;
  determining contour deviations of the inscribed joint bone from the base shape by ascertaining contour distances between the base shape and the shape of the inscribed joint bone in different incision planes;
  determining a three-dimensional deviating volume using the contour deviations; and
  using the deviating volume for correction planning.

In other words, a planning method in accordance with the invention ascertains a contour deviation not just two-dimensionally, but rather volumetrically, i.e., three-dimensionally. The method detects the part of the bone that is to be removed and/or that deviates from a desired shape. An advantage of this method is that such a volume can be easily outputted separately or in relation to the bone as an image in a computer-assisted planning system. The surgeon is thus given a three-dimensional impression of what material should be removed during the treatment. Other considerations can be made with regard to the volume of bone to be removed. If the three-dimensional deviating volume is available, it is possible to exclude particular points or partial volumes from reconstruction or to mark them as volumes that are not to be removed.

The imaging method referred to herein can be a computer tomography method, a nuclear spin tomography method, or an x-ray method comprising volumetric detection. Any possible three-dimensional modeling of the bone joint structure can be used. This modeling may also include scanning the object using other methods (for example, surface scanning).

Within the framework of the method in accordance with the invention, it is possible to determine the deviating volume by comparing the contours in incision planes that are rotated about an axis, wherein the axis is one that is characteristic of the joint bone. The method also can be used to determine the deviating volume by comparing the contours in adjacent incision planes.

The inscribed base shape can be a spherical shape, a saddle shape, a cylindrical shape or a combination of such shapes, and may be selected depending on the application. It is also possible to use a base shape for the joint bone from an anatomical atlas or a generic or statistical model that is scaled or sized accordingly. The joint bone in question can be the femoral neck bone, wherein the base shape may be a spherical shape that is inscribed into the head of the femoral neck bone.

In an exemplary application of the method, contour deviations from the spherical shape may be determined successively in a plurality of incision planes that are rotated about the femoral neck axis. The contour deviations can be determined in one incision plane or in each incision plane along a radius vector of the sphere that assumes varying angles ($\alpha$) with respect to the neck axis of the femoral neck (over a measurement range). The measurement range with respect to said angle ($\alpha$) towards the free end of the femoral head begins where the contour of the head first deviates from the base shape. In such examples, the measurement range with respect to the angle ($\alpha$) towards the femoral neck can end where the angle ($\alpha$) assumes a standard value. The standard value can be determined on the basis of an evaluation of standardized models (for example, generic or statistical shape models). The standard value can vary depending on the orientation of the incision plane. Alternatively, the measurement range can end where the angle ($\alpha$) assumes a value that corresponds to a mirrored angle ($\beta$). The mirrored angle ($\beta$) is the angle assumed by a spherical radius vector with respect to a neck axis when it points to the transition between the head of the femoral bone and the femoral neck (on the side opposite the contour deviation).

The following data concerning the deviating volume can be outputted, individually or in combination, for subsequent use or processing:
  incision planes with contour deviations and/or a base shape, including the incision plane with the greatest contour deviation;
  ascertained measurement range angles ($\alpha$, $\beta$);
  bone characteristics such as the center of rotation of the joint, the position of the neck axis, the pelvic planes, and the axial position of the femoral bone.

The data can be used in various ways. For example, it can be outputted on a display or screen, and/or provided to a medical navigation system.

In an example of the method in accordance with the invention, a reconstructed volume is calculated from the deviating volume by considering one or more of the following ancillary conditions:
  a sufficient bone depth should be maintained;
  a new shape of the joint bone should have smooth transitions and should have no indentations or minimal indentations;

a new shape of the joint bone should come as near as possible to a natural shape of the joint bone (by comparison with standard shapes);

the influence of bone interference regions is weighted depending on its critical properties;

the reconstructed volume, specifically the volume to be removed, should be minimized as far as possible.

In accordance with the invention, it is also possible to perform a method to determine a new shape of the joint bone with the aid of the deviating volume and/or reconstructed volume, and a joint movement is simulated with computer assistance. The simulation can use the new shape of the joint bone, and, on the basis of interference detection, the expected increase in the range of motion may be ascertained and outputted.

BRIEF DESCRIPTION OF THE DRAWINGS

The forgoing and other features of the invention are hereinafter discussed with reference to the figures.

DETAILED DESCRIPTION

Figure 1:
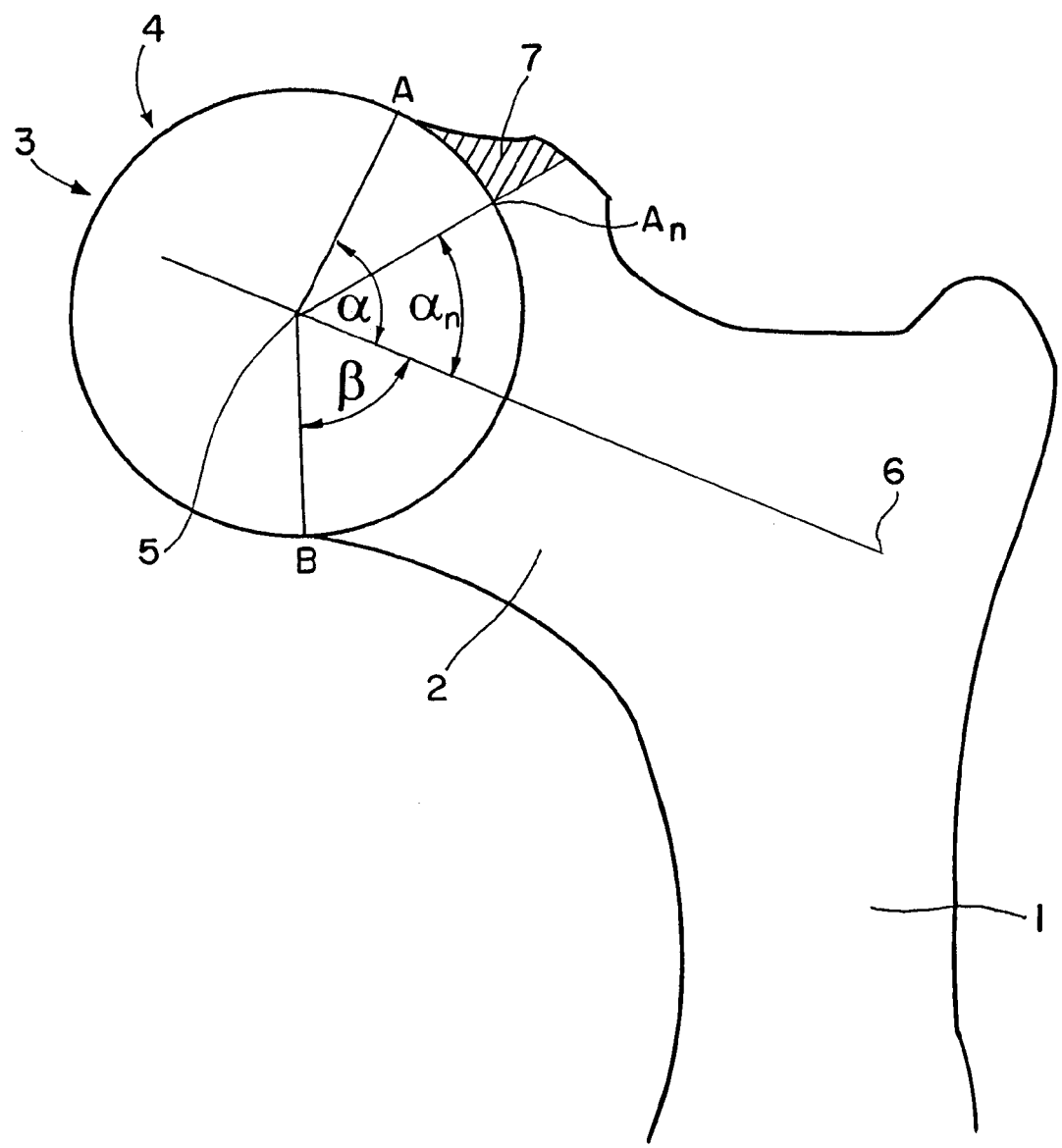
FIG. 1 is a sectional drawing through the femoral neck region, with the reconstruction planning parameters indicated.

FIG. 1 shows the neck region of a femoral bone 1, comprising a femoral neck 2 and a joint head 3. The joint head 3 has been inscribed with a sphere 4 that is shown as a circle in the sectional representation in FIG. 1. A center point 5 of the sphere 4 simultaneously forms the center point of the joint head 3 (head of the femur). Also shown in FIG. 1 are a femoral neck axis 6, and a protruding volume of bone shown as crosshatched region 7 (also known as a deviating volume), that can cause interference in the hip joint and arthritis.

To determine the deviating volume 7, particular angles are used as indicated in FIG. 1 as arcs in the circle having the center point 5. In a preoperative situation, an angle $\alpha$ indicates the angle between the neck axis 6 and a line 5-A, wherein A is the first point on the sphere at which the contour of the bone deviates from a spherical shape. An angle $\beta$ is the angle between the neck axis 6 and a line 5-B on the lower ("healthy") side of the femoral neck, wherein B is the first point on the sphere at which the contour of the bone deviates from a spherical shape. An angle $\alpha_n$ indicates the desired postoperative angle between the neck axis 6 and a line 5-$A_n$, wherein $A_n$ is the first point on the sphere where the contour of the bone deviates from a spherical shape after an operation to abrade the crosshatched bone region. The crosshatched bone region outside the circle that is between lines 5-A and 5-$A_n$ forms the deviating volume 7.

Figure 2:
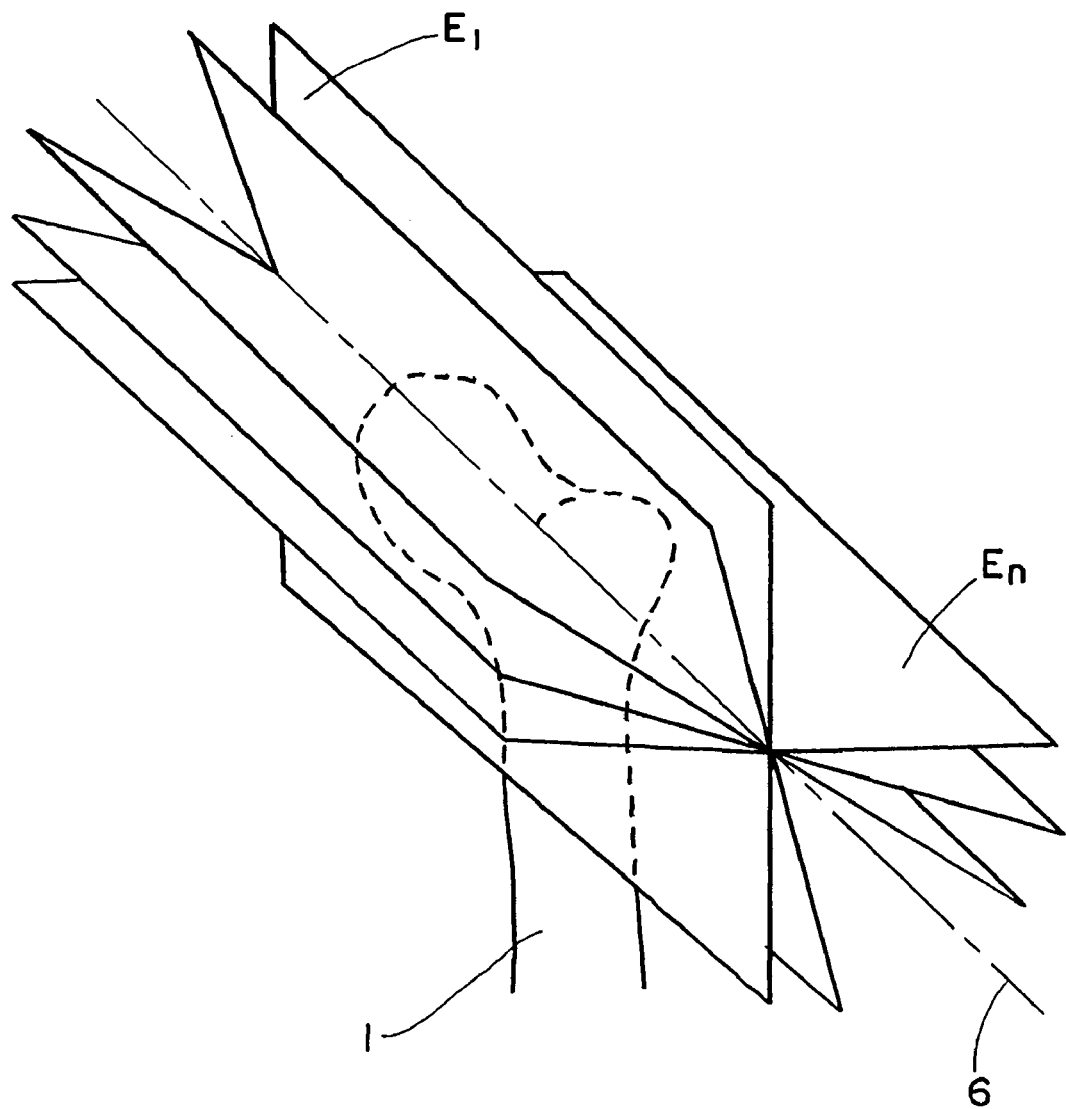
FIG. 2 is a representation of the incision planes used for determining the deviating volume.

FIG. 2 illustrates how the deviating volume is three-dimensionally determined (manually or automatically). The femoral neck axis 6 of the femoral bone 1 and a desired number of planes $E_1$ to $E_n$ (rotated about said neck axis 6) are determined (with computer assistance) from the volume image data set. For each plane reconstruction that is rotated at an angle about the neck axis 6, an analysis of the circularity of the head of the femoral neck is performed, using the parameters shown in FIG. 1. In each plane reconstruction, the angle is measured between the neck axis 6 and a point on the inscribed circle where the surface of the bone departs from a circular shape.

The plane with the maximum difference between the angles may be used to display the patient's disease pattern and to take a comparative measurement of the patient. This plane may be one of the preset reconstruction views in various display options of the software used. As already mentioned, the angle $\beta$ between the neck axis 6 and the line 5-B can be used as a target preset for reconstruction on the opposite side. Alternatively, preset standard values also can be used for this purpose. These standard values can be generated from a generic or statistical model.

Once these calculations have been made for each reconstruction or reconstruction plane, a proposed contour boundary can be ascertained and displayed, and the corresponding values can also be relayed to a navigation system to assist the treatment.

A method of reconstruction planning in accordance with the invention may be based on the following concepts:

One optional plan for reconstructing or reshaping the femoral neck may be made based on the $\alpha$ and $\beta$ angle concept described above. The concept is expanded from the previous two-dimensional approach to a three-dimensional approach. The $\beta$ angles for all of the rotated planes are mirrored from a reference side that is not to be treated onto the side that is to be treated, and these angles are used as a minimum limit for defining the volume to be removed. Alternatively, standard values ascertained on the basis of a generic or statistical shape model may be used as the minimum limit for defining the volume to be removed.

Another optional plan for reshaping the femoral neck and/or the boundary of the joint socket may be made, based on the concept of regaining range of motion. Based on an interference detection algorithm, a range-of-motion analysis may be produced using desired range-of-motion values (for example, standard values). Any regions that contribute to a bone interference are identified and taken into account in the reconstruction.

Optionally, the selected reshaping plan may be checked for depth based on a "femoral neck fracture risk concept." Using this concept, one checks to ensure that a certain amount of bone (for example, in accordance with the cortical depth) is retained during reshaping.

The overall plan can use one of these optional plans or can be optimized for a combination of the corresponding criteria. Additionally, other ancillary conditions can be incorporated into planning, including the following:

The smoothness "of the volume to be removed" (the abrasion volume) and of the remaining bone structures. This criterion should ensure that no recesses are introduced into the bone that could lead to fractures.

The natural shape (for example, curves) of the bone (for example, in accordance with a standardized bone model) should be reproduced, wherein bone anomalies would be removed.

The influence of the interference regions can be weighted, for calculating the volume to be removed. The weighting can include an estimation of how critical the corresponding interference regions may be. The critical nature of the interference regions can be estimated from the position of the region (for example, using the a angles) or from the configuration of the joint where the interference occurs (for example, comparing flexion/extension, internal/external rotation, and/or abduction/adduction with standardized values for the range of motion).

The volume, region or depth of the abrasion should be minimized in accordance with ancillary conditions. The depth values can be weighted in accordance with the reliability and severity of detected interferences or other bone anomalies. Depth values can, for example, be used to rate the frequency or severity of an interference.

Using such ancillary conditions, the volume to be removed (or reconstruction volume) can be expanded to regions that are further away from the main interference regions, for example, towards the femoral neck. These ancillary conditions may be used to ensure minimal trauma and to ensure the stability and smoothness of the bone after the surgery.

An exemplary method sequence for planning in accordance with the invention can include the following steps:

1. segmenting a CT scan (delineating the bone and tissue);
2. segmenting the obtained image material to delineate the individual bones (for example, right femur, left femur, pelvis) and to assign atlas-based properties of the bone elements (center of rotation, neck axis, femoral axis, pelvic planes);
3. checking the results and possibly optimizing the segmentation, and assigning bone characteristics (manually or automatically);
4. inscribing a base shape (for example, a sphere) into the bone (for example, joint head) (manually or automatically);
5. analyzing the anomaly parameters ($\alpha$, $\beta$ angles) three-dimensionally, using a circular analysis (for example, a "sphere test");
6. checking the depth of the volume of bone by measuring the distance between the neck axis and the surface; and outputting the depth percentage ("fracture safety value");
7. analyzing interferences (for example, using software simulation);
8. outputting parameters (for example, the increase in the range of motion, the maximum $\alpha$, $\beta$ angles, and the proposed volume of bone) wherein preset views are proposed to enable a simple assessment by the user.

If, after Step 8, the information is still insufficient, the planning was unsuccessful, or there is an additional need for optimization, the user can make corrections and run the method again, at least beginning with Step 5, until the desired result is achieved.

Figure 3:
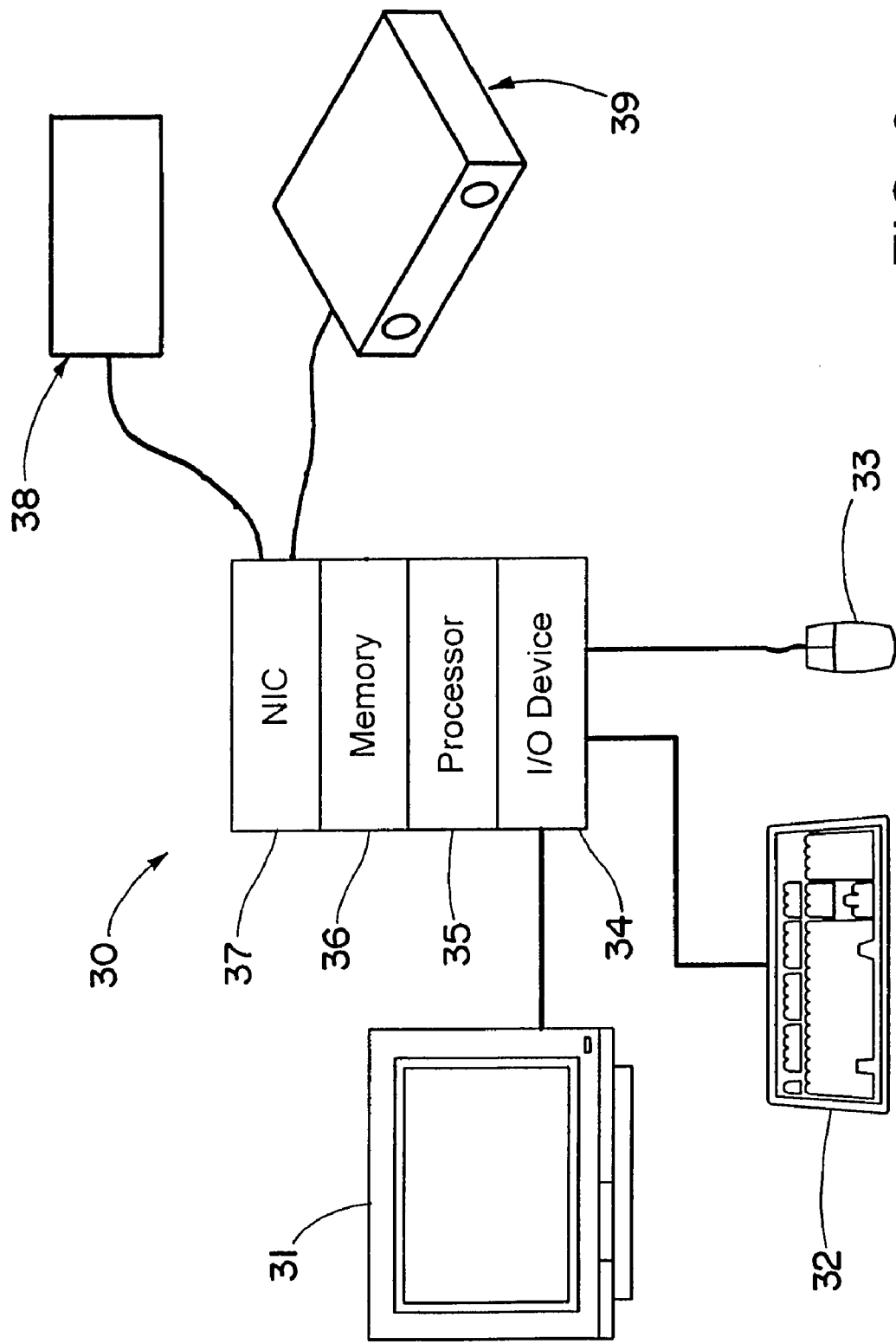
FIG. 3 illustrates a block diagram of an exemplary computer that may be used to implement one or more of the methods described herein.

Moving now to FIG. 3 there is shown a block diagram of an exemplary computer 30 that may be used to implement one or more of the methods described herein. The computer 30 may be a standalone computer, or it may be part of a medical navigation system, for example. The computer 30 may include a display or monitor 31 for viewing system information, and a keyboard 32 and pointing device 33 for data entry, screen navigation, etc. Examples of a pointing device 33 include a computer mouse or other device that points to or otherwise identifies a location, action, etc., e.g., by a point and click method or some other method. Alternatively, a touch screen (not shown) may be used in place of the keyboard 32 and pointing device 33. The display 31, keyboard 32 and mouse 33 communicate with a processor via an input/output device 34, such as a video card and/or serial port (e.g., a USB port or the like).

A processor 35, such as an AMD Athlon 64® processor or an Intel Pentium IV® processor, combined with a memory 36 execute programs to perform various functions, such as data entry, numerical calculations, screen display, system setup, etc. The memory 36 may comprise several devices, including volatile and non-volatile memory components. Accordingly, the memory 36 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 35 and the memory 36 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 37 allows the computer 30 to communicate with other devices. Such other devices may include a medical imaging device 38 and/or a medical navigation system 39.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 36 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed Figures. In particular regard to the various functions performed by the above described elements (components, assemblies, devices, software, computer programs, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of computer-assisted planning for correcting changes in the shape of joint bones in a bone joint, comprising:
    providing a three-dimensional imaging data set of a bone joint having joint bones;
    identifying the joint bones in the data set based on shapes of the joint bones in the data set and typical joint bone shapes;
    inscribing a portion of a joint bone to be reconstructed with an assignable base shape;
    determining contour deviations of the inscribed joint bone from the base shape by ascertaining contour distances between the base shape and the shape of the inscribed joint bone in different incision planes;
    determining, using a processor, a three-dimensional deviating volume using said contour deviations; and
    using said deviating volume for correction planning.

2. The method according to claim 1, wherein identifying the joint bones in the data set includes computer-assisted segmentation to identify the joint bones.

3. The method according to claim 1, wherein inscribing a portion of a joint bone includes performing graphic data processing.

4. The method according to claim 1, wherein providing the three-dimensional image data set includes producing the data set from a computer tomography method, a nuclear spin tomography method, or an x-ray method including volumetric detection.

5. The method according to claim 1, wherein determining the three-dimensional deviating volume includes comparing the contour deviations in the different incision planes that are rotated about an axis, wherein the axis is an axis of the joint bone.

6. The method according to claim 1, wherein determining the three-dimensional deviating volume includes comparing the contour deviations in adjacent incision planes.

7. The method according to claim 6, wherein the base shape is a generic or statistical model that is scaled for size.

8. The method according to claim 1, wherein the base shape comprises a spherical shape, a saddle shape, a cylindrical shape, or a combination of such shapes.

9. The method according to claim 1, wherein the base shape is a base shape for the joint bone from an anatomical atlas or other comparative model.

10. The method according to claim 1, wherein the joint bone is a femoral neck bone, and the base shape comprises a spherical shape that is inscribed into a head of the femoral neck bone.

11. The method according to claim 10, further comprising determining contour deviations successively in a plurality of incision planes that are rotated about a femoral neck axis.

12. The method according to claim 11, wherein the plurality of incision planes include each incision plane along a radius vector of the sphere that assumes a plurality of angles ($\alpha$) with respect to the neck axis of the femoral neck over a measurement range.

13. The method according to claim 12, wherein the measurement range begins where a contour of the head of the femoral neck bone first deviates from the base shape.

14. The method according to claim 12, wherein the measurement range with respect to the angle ($\alpha$) towards the femoral neck ends ($\alpha_n$) where the angle ($\alpha$) assumes a value that corresponds to a mirrored angle ($\beta$), wherein the angle ($\beta$) is the angle assumed by a spherical radius vector with respect to the neck axis when it points to the transition between the head of the femoral bone and the femoral neck, on the side opposite the contour deviation.

15. The method according to claim 10, wherein the measurement range with respect to the angle ($\alpha$) towards the femoral neck ends ($\alpha_n$) where the angle ($\alpha$) assumes a standard value that is preset, wherein the standard value can vary depending on the orientation of the incision plane.

16. The method according to claim 1, further comprising outputting at least one of:
    incision planes with contour deviations and/or a base shape;
    ascertained measurement range angles ($\alpha$, $\beta$); and/or bone characteristics.

17. The method according to claim 16, wherein the incision planes with contour deviations and/or a base shape include an incision plane having the greatest contour deviation.

18. The method according to claim 16, wherein the bone characteristics include: the center of rotation of the joint, the position of the neck axis, the pelvic planes, and/or the axial position of the femoral bone.

19. The method according to claim 16, further comprising providing the data to a medical navigation system.

20. The method according to claim 1, further comprising calculating a reconstructed volume from the deviating volume based on one or more of the following ancillary conditions:
    a sufficient bone depth should be maintained;
    a new shape of the joint bone should have smooth transitions and should have no indentations or minimal indentations;
    a new shape of the joint bone should come as near as possible to a natural shape of the joint bone;
    an influence of bones interference regions should be weighted depending on their importance to the function of the joint; and/or
    the volume to be removed should be minimized.

21. The method according to claim 1, further comprising performing a computer simulation of a joint movement based on a new shape of the joint bone and on interference detection to ascertain and output a projected range of bone joint motion.

22. A computer program embodied on a non-transitory computer readable medium for computer-assisted planning for correcting changes in the shape of joint bones in a bone joint, comprising:
    a) code that receives and stores in memory a three-dimensional imaging data set of a bone joint having joint bones;
    b) code that identifies the joint bones in the data set based on shapes of the joint bones in the data set and typical joint bone shapes;
    c) code that inscribes a portion of a joint bone to be reconstructed with an assignable base shape;
    d) code that determines contour deviations of the inscribed joint bone from the base shape by ascertaining contour distances between the base shape and the shape of the inscribed joint bone in different incision planes;
    e) code that determines a three-dimensional deviating volume using said contour deviations; and f) code that generates a correction plan using said deviating volume.

23. A system for computer-assisted planning for correcting changes in the shape of joint bones in a bone joint, comprising:

a computer operatively coupled to receive a three-dimensional imaging data set of a bone joint, said computer comprising:

a processor and memory, and logic stored in the memory and executable by the processor, said logic including:

i) logic that receives and stores in memory a three-dimensional imaging data set of a bone joint having joint bones;

ii) logic that identifies the joint bones in the data set based on shapes of the joint bones in the data set and typical joint bone shapes;

iii) logic that inscribes a portion of a joint bone to be reconstructed with an assignable base shape;

iv) logic that determines contour deviations of the inscribed joint bone from the base shape by ascertaining contour distances between the base shape and the shape of the inscribed joint bone in different incision planes;

v) logic that determines a three-dimensional deviating volume using said contour deviations; and vi) logic that generates a correction plan using said deviating volume.

* * * * *